(12) United States Patent
Crudge et al.

(10) Patent No.: US 7,663,005 B2
(45) Date of Patent: Feb. 16, 2010

(54) PROCESS FOR PREPARING AN ALKYLENE GLYCOL

(75) Inventors: William Crudge, Upper Saddle River, NJ (US); Jaap Willem van Hal, Fresno, TX (US); Xiankuan Zhang, Houston, TX (US)

(73) Assignee: SD Lizenzverwertungsgesellschaft mbH & Co. KG, Munich (DE)

( * ) Notice: Subject to any disclaimer, the term of this patent is extended or adjusted under 35 U.S.C. 154(b) by 0 days.

(21) Appl. No.: 11/755,464

(22) Filed: May 30, 2007

(65) Prior Publication Data

US 2008/0300431 A1    Dec. 4, 2008

(51) Int. Cl.
*C07C 29/10*    (2006.01)
(52) U.S. Cl. ..................................... 568/867
(58) Field of Classification Search ............... 568/867
See application file for complete search history.

(56) References Cited

U.S. PATENT DOCUMENTS

| | | | |
|---|---|---|---|
| 5,466,836 A | 11/1995 | Jubin, Jr. | |
| 5,488,184 A | 1/1996 | Reman et al. | |
| 6,156,942 A | * 12/2000 | Lemanski et al. | ........... 568/867 |
| 6,160,187 A | 12/2000 | Strickler et al. | |
| 6,316,571 B1 | 11/2001 | Van Kruchten | |
| 6,580,008 B2 | 6/2003 | Van Kruchten et al. | |
| 7,105,710 B2 | 9/2006 | Boons et al. | |
| 2006/0183927 A1 | 8/2006 | Billing et al. | |

FOREIGN PATENT DOCUMENTS

| | | |
|---|---|---|
| EP | 156449 | 2/1985 |
| JP | 57139026 | 8/1982 |
| RU | 2001901 | 10/1993 |
| RU | 2002726 | 11/1993 |
| RU | 2284985 | 10/2006 |
| WO | 9520559 | 8/1995 |
| WO | 9733850 | 9/1997 |

* cited by examiner

*Primary Examiner*—Elvis O Price
(74) *Attorney, Agent, or Firm*—Scully, Scott, Murphy & Presser, P.C.

(57) ABSTRACT

A catalytic process for preparing a monoalkylene glycol from a corresponding alkylene oxide utilizing an ion exchange resin and a reactor in which an upflow process is used is provided. In particular, the process includes reacting water and an alkylene oxide in at least one reactor under conditions to form an alkylene glycol, wherein the at least one reactor includes an ion exchange resin and the reactor is operating in an upflow direction.

22 Claims, 2 Drawing Sheets

PROCESS FOR PREPARING AN ALKYLENE GLYCOL

FIELD OF THE INVENTION

The present invention relates to a process for preparing an alkylene glycol from an alkylene oxide. More particularly, the present invention provides a process for preparing monoethylene glycol from ethylene oxide utilizing a catalyst based on an ion exchange resin.

BACKGROUND OF THE INVENTION

Alkylene glycols, such as monoalkylene gycols, are of continued commercial interest and the demand for the same has increased. For example, monoalkylene glycols are used in anti-freeze compositions, as solvents and as base materials in the production of polyalkylene terephthalates, e.g., for fibers and bottles.

Alkylene glycols are typically prepared from their corresponding alkylene oxide utilizing a liquid phase hydrolysis process. In commercial production, the hydrolysis reaction is performed without a catalyst by adding a large excess of water, e.g., 15 to 30 moles of water per mole of alkylene oxide. The prior art hydrolysis reaction is a nucleophilic substitution reaction, in which ring opening of the alkylene oxide occurs and water serves as the nucleophile.

Because initially formed monoalkylene glycol also acts as a nucleopile, a mixture of monoalkylene glycol, dialkylene glycol and higher alkylene glycols is typically formed. In order to increase the selectivity to monoalkylene glycol, it is necessary to suppress the secondary reaction between the primary product and the alkylene oxide, which competes with the hydrolysis of the alkylene oxide.

One effective technique for suppressing the secondary reaction is to increase the amount of water present in the reaction mixture. Although this prior art technique improves the selectivity towards the production of the monoalkylene glycol, it creates a problem in that large amounts of water have to be removed. Removing such additional water increases production costs because such a removal process is energy intensive and requires large-scale evaporation/distillation facilities.

A number of prior art publications show that higher selectivity to monoalkylene glycols can be achieved if the reactions are conducted using heterogeneous catalytic processes, such as, for example, with catalysts based on an ion exchange resin as disclosed in EP-A-156,449 (metalate-containing anion exchange resins); JP-A-57-139026 (anion-exchange resin in the halogen form); Russian Patent Nos. 2002726 and 2001901 (anion exchange resin in the bicarbonate form); WO/20559A (anion exchange resin); and WO 97/33850 (anion exchange resin).

The literature also describes various reactor arrangements that can be used in such catalytic processes. For example, U.S. Pat. No. 6,160,187 describes several arrangements of an adiabatic reactor in combination with heat exchangers. In accordance with the '187 patent, a downflow operation is preferred over an upflow operation since downflow operations reportedly have specific advantages over an upflow process.

Despite all of the advances made in the catalytic hydrolysis of alkylene oxides, there is a continued need for providing a new and improved process of producing monoalkylene glycol from the corresponding alkylene oxides.

SUMMARY OF THE INVENTION

In view of the above, the present invention provides an improved catalytic process for preparing an alkylene glycol from the corresponding alkylene oxide utilizing a catalyst based on an ion exchange resin and a reactor in which an upflow process is used. In some embodiments of the present invention, the upflow process can be used to aid in replacing all, or a portion, of the catalyst bed.

There is an advantage in being able to remove a portion of the catalyst used periodically and to replace it either with fresh or regenerated catalyst during operation. This avoids the need to shut down the reactor to change the catalyst, so it is particularly advantageous with a relatively-short lived catalyst. Shutting down the reactor will cause loss of production unless some arrangements are made, for example, by adding a spare reactor at an additional cost. In particular, catalysts based on ion exchange resins are known to swell under ethylene oxide hydrolysis conditions, and the ability to replace swollen resins beads further helps by limiting the extent that the bed volume increases with time on stream.

In the present invention, catalyst removal and replacement can be aided by an upflow operation when the upward velocity is sufficient to expand or fluidize the catalyst bed. Partial or complete segregation of catalyst particles by size in an expanded bed can also be advantageous in allowing selective removal of the most swollen particles.

In general terms, the present invention provides a catalytic hydrolysis process of converting an alkylene oxide, preferably ethylene oxide, into its corresponding alkylene glycol, preferably monoethylene glycol. The inventive method comprises:

reacting water and an alkylene oxide in at least one reactor under conditions to form an alkylene glycol, wherein said at least one reactor includes a catalyst based on an ion exchange resin and said reactor is operating in an upflow direction.

By "upflow" direction it is meant that the reactants, i.e., water and alkylene oxide, as well as catalyst particles that are produced during the use of the catalyst are traveling in a direction from the bottom of the reactor upwards. It has been observed that by using an upflow operation, the catalyst employed has an extended lifetime, for example, an improved lifetime of up to 2 times greater has been observed, than that exhibited for a downflow operation. In a downflow operation, the pressure drop due to liquid flow tends to compact the catalyst bed and prevent movement of catalyst particles. In an upflow operation, the pressure drop acts to counter the weight of the catalyst particles, and if the pressure drop is sufficiently high it can allow catalytic particles to move and increase the void space between particles.

Another benefit of the inventive process is that small contaminate particles, e.g., catalyst fragments (resin beads that break off during operation), can be removed from the reactor during use. When a downflow operation is employed, these contaminate particles can become trapped within the catalyst bed. When an upflow operation is used, the small contaminate particles can be removed by the upward flow of liquid, helped by the ability of catalyst particles to move and by the higher void space.

A still further benefit of the inventive process is that the pressure drop within the system is limited to what is needed to support the catalyst bed. In a downflow operation, an increased pressure drop increases the chance of mechanical damage to the catalyst particles.

DETAILED DESCRIPTION OF THE INVENTION

The present invention, which provides a catalytic hydrolysis process for producing an alkylene glycol from an alkylene oxide, particularly, monoethylene glycol from ethylene oxide, utilizing a catalyst based on an ion exchange resin and a reactor that operates in an upflow direction, will now be described in greater detail by referring to the following discussion and drawings that accompany the present application. It is noted that the drawings of the present application are provided for illustrative purposes and, as such, they are not drawn to scale.

As stated above, the present invention provides a catalytic hydrolysis process for preparing an alkylene glycol by reacting alkylene oxide and water in presence of an ion exchange resin. The ion exchange resin is employed in the present invention as a heterogeneous catalyst for converting an alkylene oxide into its corresponding monoalkylene glycol.

The term "alkylene" is used in the present invention to denote an organic radical formed from an unsaturated aliphatic hydrocarbon typically having from 2 to 22 carbon atoms, preferably 2 to 6 carbon atoms. The preferred alkylene oxides that are employed in the present invention include ethylene oxide (EO), propylene oxide (PO), and butylene oxide (BO). The preferred alkylene glycols include their respective monoalkylene glycols: monoethylene glycol (MEG), monopropylene glycol (MPG), and monobutylene glycol (MBG). Most preferably, the present invention provides a method for preparing MEG from ethylene oxide and water.

The hydrolysis reaction employed in the present invention is performed in any type of reactor including, for example, an adiabatic reactor and/or a non-adiabatic reactor. Preferably, a non-adiabatic reactor is used. By "non-adiabatic" it is meant that substantial transfer of heat occurs to, or from, the reactor system. Thus, the reactor systems employed in some embodiments of the present invention include at least one means for removing/transferring heat to and from the system. Such means for removing/transferring heat are well known to those skilled in the art. In one embodiment of the present invention, the non-adiabatic reactor includes a heating/cooling jacket that is wrapped around the outside of the reactor.

Figure 1:
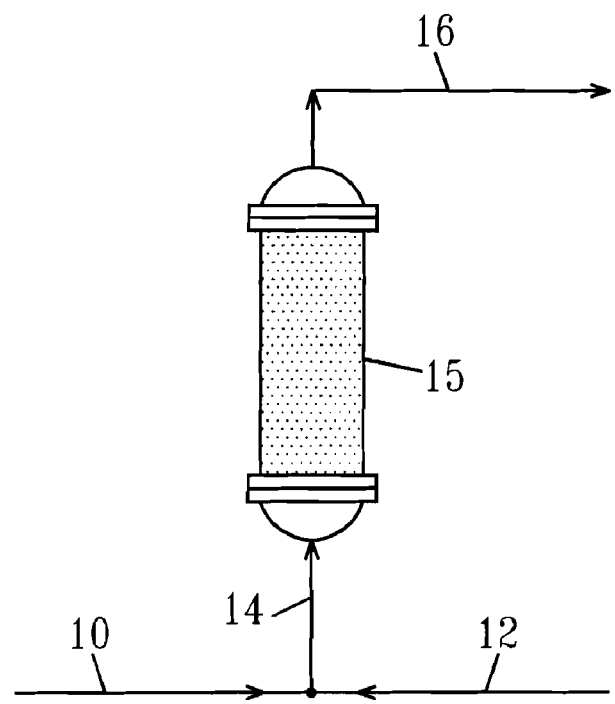
FIGS. 1-3 illustrates some examples of reactors that can be employed in the present invention.
Figure 2:
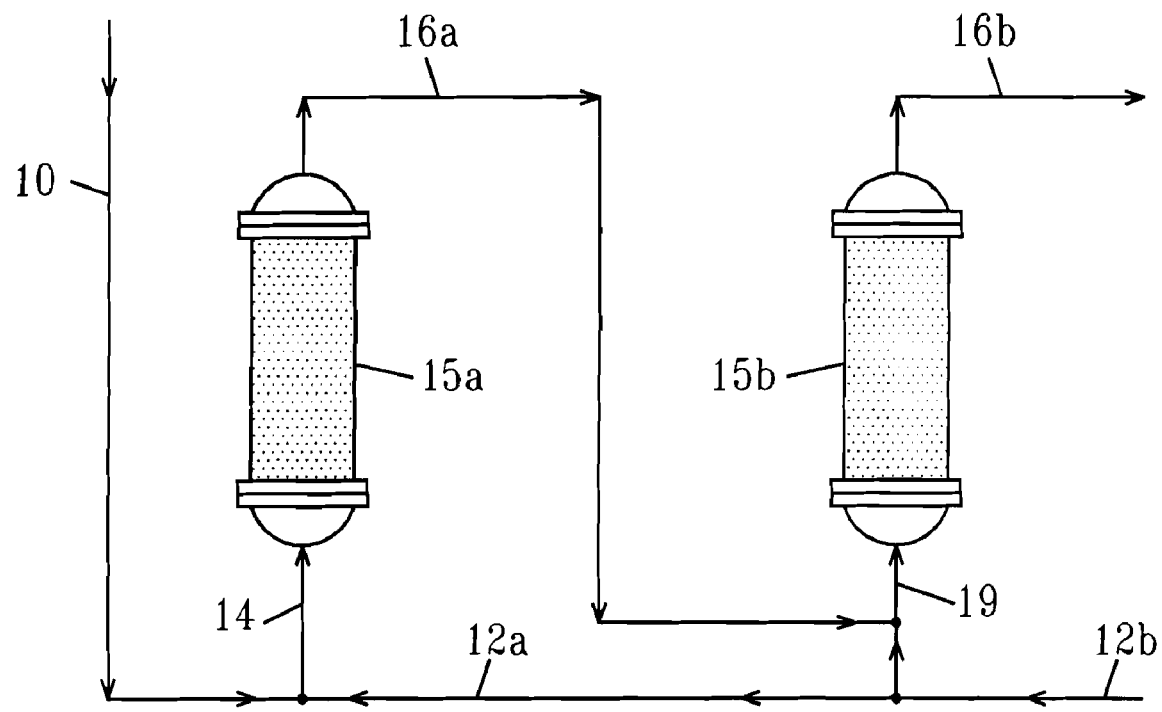
Figure 3:
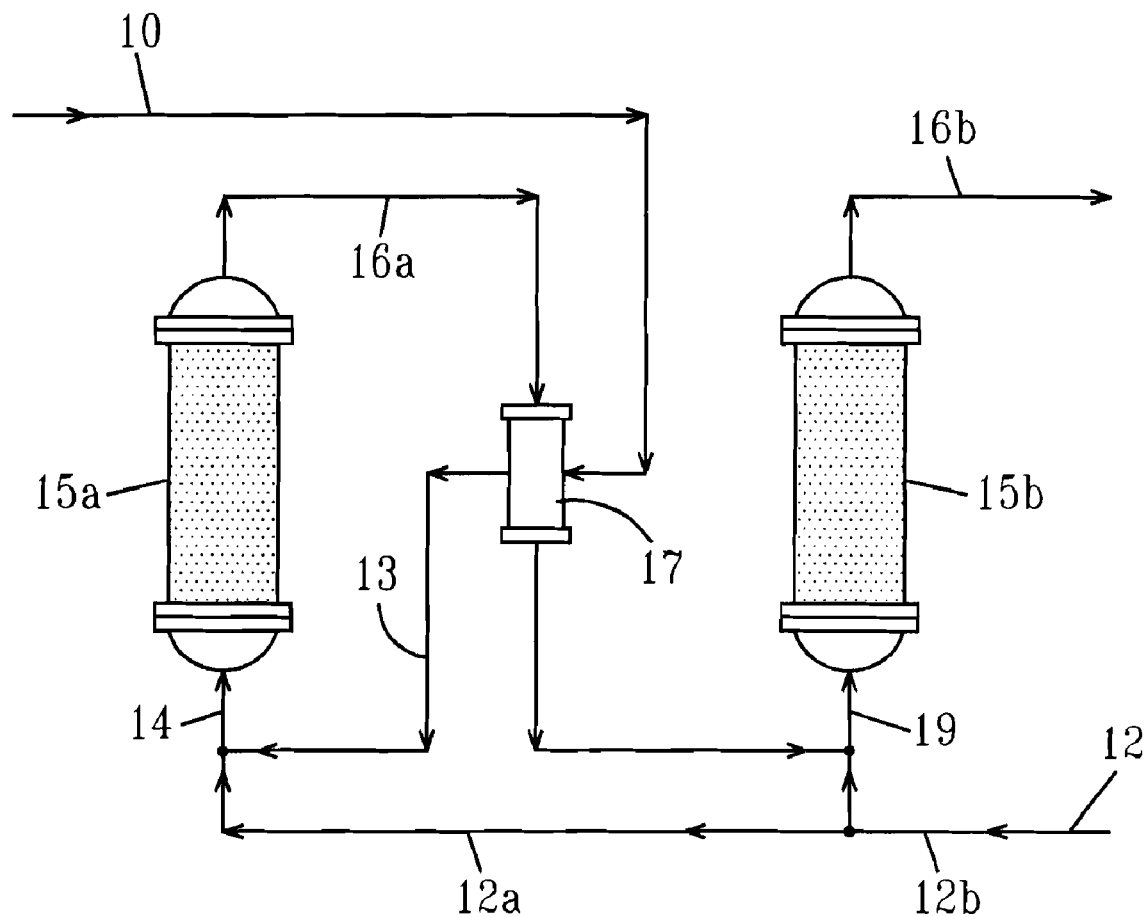

Illustrations of various configurations of the reactor systems that may be employed in the present application are provided in FIGS. 1-3. It is noted that FIGS. 1-3 include some basic reactor systems that can be employed. Other reactor systems that can operate in an upflow direction are also contemplated and, as such, the present invention is not limited to the reactor systems shown herein. To avoid obscuring the reactor, the means for removing/transferring heat, required when a non-adiabatic reactor is employed, is not shown.

In FIGS. 1-3, the following reference numerals are used: 10 denotes a water feed; 12 denotes an alkylene oxide feed; 13 denotes a heated water feed (after being cross-exchanged); 14 denotes a combined water and alkylene oxide feed; 15 denotes a reactor; 16 denotes a product stream; 17 denotes a heat exchanger; and 19 denotes a combined product and alkylene oxide feed.

Specifically, FIG. 1 illustrates a single catalytic reactor. Water feed 10 is combined with an alkylene oxide feed 12 and fed to a reactor 15 as a combined water and alkylene oxide feed 14. The water and alkylene oxide react in the reactor 15 and in the presence of a catalyst to form a glycol product stream 16. In the reactor designs shown, the heat exchanging means is sometimes not shown so as not to complicate the drawings.

As mentioned above, it is known that ion exchange processes and solvents cause ion exchange resins, particularly anion exchange resins, to swell. This type of swelling is reversible, and the extent of swelling is limited. However, under conditions of alkylene oxide hydrolysis, especially EO hydrolysis, anion exchange resins unexpectedly swell continuously and irreversibly to an unlimited extent. Such continuous, unlimited swelling can create problems in an industrial situation, such as reactor plugging and a detrimental effect on selectivity.

The reactors employed allow unconstrained expansion of the resin catalyst; otherwise, the resin will expand against the walls of the reactor, plugging off flow through the catalyst bed and generating very high pressures that could rupture the reactor and reduce the flow of fluid through the bed. This requires that the reactor volume be greater than the initial volume of the resin bed and that the shape and/or proportions of the reactor and/or catalyst bed be such that the resin can expand freely into the portion of the reactor that does not initially contain catalyst, without binding or bridging against the reactor walls. These requirements can be met by using, for example, a vertical cylindrical vessel for the reactor, with a sufficiently low height to diameter ratio of the catalyst bed. In such a reactor, the catalyst could be located at the bottom portion of the vessel and allowed to expand upward over time.

Preferably, the height to width ratio of the catalyst bed in the reactor is greater than 1, and more preferably greater than about 1 to less than or equal to about 20:1. Preferably, the height to width ratio of the catalyst bed in the reactor is at least about 0.1:1, and more preferably at least about 0.5:1.

Another type of reactor configuration that allows for unconstrained resin swelling is a vessel with one or more conical shaped sections, where the reactor diameter either increases or decreases continuously from the bottom to the top of a conical section, and the angle of inclination of a conical section is such that the resin can expand upward freely by minimizing friction and lateral forces against the reactor wall. The reactor may have short cylindrical sections at the inlet and outlet and also between conical sections, if there is more than one conical section. The angle of inclination of a conical section necessary to allow the resin to expand freely is determined by the properties of the catalyst bed. Preferably, the angle of inclination is at least 1° from vertical, and more preferably at least about 5° from vertical. Preferably the angle of inclination is less than or equal to about 45° from vertical, and more preferably less than or equal to about 35° from vertical. Other than for economical considerations, this reactor configuration has no upper limit on the ratio of height to width, as there is for a vertical cylindrical vessel.

Yet another type of reaction vessel is a combination of cylindrical shaped sections having either increasing or decreasing diameter from bottom to top. In this manner, a small diameter cylindrically shaped lower section is connected to one or more cylindrically shaped sections of increasing diameter, such that the diameter increases discretely from the bottom to the top of the vessel.

The cylindrical and conical reactor configurations mentioned above are only examples of reactors that allow unconstrained resin expansion, and the present invention is not limited to those configurations. Instead, other configurations such as vertical reactors are possible that meet the requirements for unconstrained resin expansion.

In the present invention, the reaction mixture (i.e., reactants; water and alkylene oxide) is fed to the bottom of the reactor. The reaction mixture then flows upward through the catalyst bed, where it reacts and forms glycol product, then immediately exits the reactor In accordance with the present invention, an upflow operation is performed within the reactor. The upflow operation employed in the present invention is achieved by feeding liquid into the bottom of the reactor and removing liquid as well as catalyst particles from the top of the reactor. In accordance with the present invention and as explained above, the upflow operation can aid in replacing all or a portion of the ion exchange resin. This is achieved on line or on stream without the need of shutting down the reactor. Such an on-line or on-stream replacement is not typically possible with a downflow process.

FIG. 2 illustrates another reactor system which includes two catalytic reactors in series. The heat exchanging means are not shown for clarity. Alkylene oxide feed 12 is split into streams 12a and 12b. Water feed 10 is combined with the alkylene oxide feed 12a and fed to the reactor 15a as a combined water and alkylene oxide feed 14. The water and alkylene oxide react in the reactor 15a to form a first product stream 16a. Stream 16a is combined with alkylene oxide feed 12b and fed as combined product and alkylene oxide feed stream 19 to the second reactor 15b, where further reaction occurs to produce second product stream 16b.

In some embodiments a reactor system comprising at least two reactors in series, wherein each reactor is separated by at least one heat exchanger, is employed. Such a system is illustrated in FIG. 3, which depicts two catalytic reactors with a heat exchanger between them. In this embodiment, water feed 10 is fed to a heat exchanger 17 where it is heated with a first glycol product stream 16a from the first reactor 15a. Alkylene oxide feed 12 is divided into two feed streams. Heated water feed stream 13 is combined with the alkylene oxide feed 12a and fed to the first reactor 15a as a combined water and alkylene oxide feed 14. The water and alkylene oxide react in the first reactor 15a to form glycol product stream 16a. Stream 16a exits the reactor and is fed to heat exchanger 7 where it is cooled by cross-exchanging with water feed 10. The cooled glycol product stream is then combined with alkylene oxide feed 12b and fed as stream 19 to the second reactor 15b, where further reaction occurs to produce the second glycol product stream 16b.

In the present invention, at least one of the reactors in series must contain a catalyst bed comprising a heterogeneous catalyst based on an ion exchange resin that is capable of performing a hydrolysis reaction. If one of the reactors contains a catalyst bed ("catalytic reactor"), and it is followed in series by a reactor that does not contain a catalyst bed ("noncatalytic reactor"), another embodiment of this invention is, optionally, not to have a heat exchanger separating the catalytic reactor and the noncatalytic reactor.

The water that is employed in the present invention may be of different purity. Examples of types of water that can be used as one of the hydrolysis reactants include: deionized water, steam distilled water, condensate water (which may contain some residual glycol compounds), and also recycled water recovered from the dehydration process in the production of alkylene oxide and alkylene glycol (which may contain residual glycol).

Water is provided in an amount which is in a stoichiometric excess of that required for forming a desired glycol from reaction with alkylene oxide. Preferably, the molar feed ratio of water to alkylene oxide is at least about 1.1, more preferably at least about 2.0, and even more preferably at least about 5.0. Preferably, the molar feed ratio is no more than about 30, more preferably no more than about 25, and even more preferably no more than about 20. One skilled in the art will recognize that this ratio will vary depending upon the alkylene oxide employed, the reaction conditions, and the specific catalyst utilized.

As indicated above, water and alkylene oxide feed may be fed to the first reactor separately or together as a co-feed. Preferably, water and alkylene are co-fed into the first reactor. The water and alkylene oxide are fed to the reactors as a liquid.

The first step of the inventive process comprises feeding water and alkylene oxide into a first reactor under conditions such that the alkylene oxide and water react to form a glycol product stream comprising a glycol and water. For purposes of this invention, the "glycol product stream" denotes any product stream exiting the reactor which contains at least glycol and water. The glycol product is generally in mixture, solution, or contained within unreacted water.

Conditions which are conducive for the reaction to occur are well known to those skilled in the art and may vary depending on the type of catalysts used as well as the type of reactor used. Factors for consideration include the optimum temperature, pressure, and water to alkylene oxide ratio for reacting the feed stream(s) without providing conditions, which significantly degrade the catalyst bed or selectivity to the desired product.

The reaction temperature in reactors containing the catalyst bed is from about 30° C. to about 160° C., and preferably from about 50° C. to about 150° C. When a temperature sensitive ion exchange resin is employed, it has been determined that the lifetime of the resin is sufficiently maintained when the temperature of the reaction is kept below 100° C.; a temperature sensitive ion exchange resin can still be employed when the temperature is greater than 100° C. but the lifetime of such a resin may be reduced when operating at higher temperatures. The reaction pressure may vary depending on the reaction temperature employed as well as the composition that is fed into the reactor. The pressure is however high enough to avoid vapor formation. The selection of an appropriate reaction pressure is within the knowledge of one skilled in the art.

As set forth hereinabove, a catalyst bed must be included in at least one of the reactors in series. Typically the catalyst bed is a fixed catalyst bed which can become fluidized or expand under operation. The catalyst bed may comprise any material capable of catalyzing the desired reaction in the reactor in which it is employed. It should be of such a nature as to allow reactants and products to pass through the bed, yet provide a sufficient surface area for catalytic contact. Desirably, the catalytic material is solid and is insoluble in either the reactants or the glycol products under the conditions in the process.

Catalysts that may be employed in the present process are known in the art. Preferred catalysts are those comprising an ion exchange resin as a solid support, in particular the strongly basic (anionic) ion exchange resin wherein the basic groups are quaternary ammonium or quaternary phosphonium. The ion exchange resins may be based on the copolymer of styrene and divinylbenzene, vinylpyridine, polysiloxanes, as well as other solid supports having electropositive complexing sites of an inorganic nature, such as carbon, silica, silica-alumina, zeolites, glass and clays such as hydrotalcite. Further, immobilized complexing macrocycles such as crown ethers, etc. can be used as well as a solid support.

Preferably, the catalyst is based on a strongly basic quaternary ammonium resin or a quaternary phosphonium resin.

Examples of commercially available anion exchange resins on which the catalyst of the present invention may be based include, but are not limited to, LEWATIT® M 500, DUOLITE® A 368 and AMBERJET® 4200, DOWEX® MSA-1, MARATHON®-A and MARATHON®-MSA (all based on polystyrene resins, cross-linked with divinyl benzene) and Reillex HPQ (based on a polyvinylpyridine resin, cross-linked with divinyl benzene).

More preferably, the catalyst is based on a strongly basic quaternary ammonium resin that includes polystyrene that is cross-linked with divinyl benzene.

The anion exchange resin in the fixed bed of solid catalyst may comprise more than one anion. Preferably, the anion is selected from the group of bicarbonate, bisulfite, metalate and carboxylate anions.

When the anion is a carboxylate anion, it is preferred that the anion is a polycarboxylic acid anion having in its chain molecule one or more carboxyl groups and one or more carboxylate groups, the individual carboxyl and/or carboxylate groups being separated from each other in the chain molecule by a separating group consisting of at least one atom. Preferably the polycarboxylic acid anion is a citric acid derivative, more preferably a mono-anion of citric acid. Most preferably the anion is a bicarbonate anion.

A solid catalyst which has given particularly good results when employed in the process of the present invention, is a catalyst based on a quaternary ammonium resin, preferably a resin comprising a trimethylbenzyl ammonium group, and wherein the anion is a bicarbonate anion.

The reaction may also be conducted in the presence of carbon dioxide. Whether to provide carbon dioxide to the reaction may depend on whether a catalyst is utilized in the reactor and the type of catalyst used. For example, if an anion exchange resin is utilized as a catalyst it may be desirable to provide an amount of carbon dioxide to the catalyst bed. The carbon dioxide may be provided to the reaction in any convenient manner. The carbon dioxide may, for instance, be introduced separately and/or with one or more of the feed streams. The carbon dioxide may be present in the reaction mixture in gaseous form or in the form of carbonic acid or in the form of salts of carbonic acid. Preferably, the carbon dioxide is present in the reaction mixture in an amount less than, or equal to, 0.1 wt %, preferably 0.05 wt %, more preferably 0.01 wt %.

The reaction of this invention may also be conducted in the presence of a pH adjusting additive. Whether to provide a pH adjusting additive to the reaction may be driven by factors such as the type of catalyst used, and whether carbon dioxide is fed to the catalyst bed. For example, if the bicarbonate form of an anion exchange resin is utilized as a catalyst, it may be desirable to provide an amount of pH adjusting additive to the catalyst bed. Such additives typically comprise any organic or inorganic bases such as alkylamines, pyridine, alkali phosphates, alkali sulphates, alkali carbonates, alkali metal hydroxide, and combinations thereof. "Bases", as used herein, shall be defined as compounds that, when added to water, give a pH of greater than 7.0. Preferably, the pH adjusting additive comprises sodium hydroxide (NaOH). The pH adjusting additive is provided in an amount sufficient to maintain a pH of the reaction mixture at a lower limit of about 5.0, more preferably 5.5, and most preferably 6.0. For an upper pH limit, the pH adjusting additive is provided in an amount sufficient to maintain a pH of the reaction mixture below about 9.0, preferably 8.0, and more preferably 7.0. By referring to "pH of the reaction mixture" it is meant the pH of the mixture which includes each of the components which are fed to the reactor.

The following example is provided to illustrate the present invention and to demonstrate some advantages that can be achieved when using the same.

EXAMPLE

In this example, monoethylene glycol (MEG) was prepared by the catalytic hydrolysis of water and ethylene oxide (EO) in the presence of LEWATIT® MP 500 as the catalyst. A non-adiabatic reactor including a heating/cooling jacket operating in an upflow direction was employed. The catalyst load used in the example was 15 ml, the water to EO ratio was 8:1 by wt., the liquid feed flow rate was 1.2 ml per minute, the reaction temperature was about 130° C. and the reaction pressure was 210 psig.

For comparison, the same catalyst, same catalyst load, same water to EQ ratio, same liquid flow rate, same temperature and same pressure were used but instead of operating in an upflow direction, a downflow direction was employed.

Table 1 provides data for the upflow operation which is representative of the present invention, while Table 2 provides data for the downflow direction (not representative of the present invention). In each table TOS stands for time on stream.

TABLE 1

Upflow Operation

| TOS (hour) | Conversion (%) | Selectivity (%) |
|---|---|---|
| 1.8 | 100 | 98 |
| 19.6 | 100 | 97 |
| 21.6 | 100 | 97 |
| 25.6 | 100 | 97 |
| 41.0 | 100 | 95 |
| 42.6 | 100 | 95 |
| 44.9 | 100 | 95 |
| 47.0 | 100 | 95 |
| 49.0 | 100 | 94 |
| 64.7 | 100 | 93 |
| 68.6 | 100 | 93 |
| 70.8 | 100 | 93 |
| 73.6 | 100 | 94 |
| 90.2 | 100 | 90 |
| 91.9 | 100 | 90 |
| 94.0 | 100 | 89 |
| 96.1 | 100 | 89 |

TABLE 2

Downflow Operation

| TOS (hour) | Conversion (%) | Selectivity (%) |
|---|---|---|
| 1.8 | 100 | 98 |
| 3.8 | 100 | 98 |
| 5.8 | 100 | 97 |
| 19.8 | 100 | 95 |
| 21.8 | 100 | 95 |
| 23.8 | 100 | 95 |
| 25.8 | 100 | 94 |
| 27.8 | 100 | 94 |
| 29.8 | 100 | 93 |
| 44.2 | 100 | 90 |
| 45.8 | 100 | 89 |
| 47.8 | 100 | 89 |
| 49.8 | 100 | 89 |
| 51.8 | 100 | 89 |
| 53.8 | 100 | 88 |
| 68.1 | 100 | 87 |

The data in the two tables illustrate that the upflow operation exhibited a slower decline in selectivity as compared to the downflow operation. Additionally, the data also exhibited that the upflow operation can be performed for a longer time, i.e., increased catalyst lifetime, as compared to that of the downflow operation.

While the present invention has been particularly shown and described with respect to preferred embodiments thereof, it will be understood by those skilled in the art that the foregoing and other changes in forms and details may be made without departing from the spirit and scope of the present invention. It is therefore intended that the present invention not be limited to the exact forms and details described and illustrated, but fall within the scope of the appended claims.

What is claimed as new is:

1. A process of preparing an alkylene glycol comprising: reacting water and an alkylene oxide in at least one continuous flow reactor under conditions to form an alkylene glycol, wherein said at least one continuous flow reactor includes a catalyst bed based on an ion exchange resin whose expansion is not constrained and said reactor is operating in an upflow direction at an upward velocity sufficient to expand or fluidize the catalyst bed, said upflow direction provides a catalyst lifetime that is up to two times greater than that obtained from a downflow operation.

2. The process of claim 1 wherein said at least one continuous flow reactor uses a fluidized catalyst bed and said upflow direction aids in replacing all or a portion of said ion exchange resin during operation of said reactor.

3. The process of claim 1 wherein said ion exchange resin is a strongly basic quaternary ammonium resin or a quaternary phosphonium resin.

4. The process of claim 1 wherein said ion exchange resin includes a catalyst anion, said catalyst anion is one of bicarbonate, carboxylate, bisulphate, and a metallate anion.

5. The process of claim 1 wherein said ion exchange resin is a strongly basic quaternary ammonium resin that includes polystyrene cross linked with divinyl benzene.

6. The process of claim 1 wherein said water is present in a molar feed ratio of water to alkylene oxide of at least about 1.1, but not more than 30.

7. The process of claim 1 wherein said alkylene oxide is ethylene oxide (EG), propylene oxide (PO) or butylene oxide (BO).

8. The process of claim 1 wherein said alkylene glycol is monoethylene glycol (MEG), monopropylene glycol (MPG) or monobutylene glycol (MBG).

9. The process of claim 1 wherein said alkylene oxide is ethylene oxide and said alkylene glycol is monoethylene glycol.

10. The process of claim 1 wherein said reacting is performed at a temperature from about 30° C. to about 160° C.

11. The process of claim 1 wherein said reacting is performed at a temperature of less than 100° C. and said ion exchange resin is temperature sensitive.

12. A process of preparing monoethylene glycol comprising: reacting water and ethylene oxide in at least one continuous flow reactor under conditions to form monoethylene glycol, wherein said at least one continuous flow reactor includes a catalyst bed based on an ion exchange resin including polystyrene cross-linked with divinyl benzene, where an expansion of said ion exchange resin is not constrained and said reactor is operating in an upflow direction at an upward velocity sufficient to expand or fluidize the catalyst bed, said upflow direction provides a catalyst lifetime that is up to two times greater than that obtained from a downflow operation.

13. The process of claim 12 wherein said ion exchange resin is a strongly basic quaternary ammonium resin.

14. The process of claim 12 wherein said water is present in a molar feed ratio of water to ethylene oxide of at least about 1.1, but not more than 30.

15. The process of claim 12 wherein said reacting is performed at a temperature from about 30° C. to about 160° C.

16. The process of claim 12 wherein said reacting is performed at a temperature of less than 100° C. and said ion exchange resin is temperature sensitive.

17. The process of claim 12 wherein said at least one continuous flow reactor uses a fluidized catalyst bed and said upflow direction aids in replacing all or a portion of said ion exchange resin during operation of said reactor.

18. The process of claim 12 wherein said ethylene oxide is a gas made from an ethylene oxide reactor.

19. The process of claim 4 wherein the water and the alkylene oxide are reacted in the presence of carbon dioxide.

20. The process of claim 1, wherein the water comprises recycled water.

21. The process of claim 12, wherein the water comprises recycled water.

22. The process of claim 12 wherein said ion exchange resin includes a catalyst anion, said catalyst anion is one of bicarbonate, carboxylate, bisulphate, and a metallate anion and wherein the water and the alkylene oxide are reacted in the presence of carbon dioxide.

* * * * *